United States Patent [19]

Gauthier et al.

[11] 4,307,092

[45] Dec. 22, 1981

[54] 1-OXO-5H-PYRIMIDO[2,1-C]BENZOXA-ZINE-2-CARBOXYLIC ACID ESTERS

[75] Inventors: Jean A. Gauthier; Ivo L. Jirkovsky, both of Montreal, Canada

[73] Assignee: Ayerst McKenna & Harrison, Inc., Montreal, Canada

[21] Appl. No.: 173,507

[22] Filed: Jul. 22, 1980

Related U.S. Application Data

[62] Division of Ser. No. 65,790, Aug. 13, 1979, Pat. No. 4,254,118.

[51] Int. Cl.$^3$ ................ C07D 513/04; A61K 31/505; A61K 31/495; C07D 487/04
[52] U.S. Cl. ............................ 424/248.55; 544/101
[58] Field of Search .................. 544/101; 424/248.55

[56] References Cited

U.S. PATENT DOCUMENTS 4,066,766  1/1978  Kadin .................................. 424/251
4,207,318  6/1980  Rowlands et al. .................. 544/101

*Primary Examiner*—John M. Ford
*Attorney, Agent, or Firm*—Arthur E. Wilfond

[57] ABSTRACT

This invention discloses novel 1-oxo-5H-pyrimidol[2,1-c][1,4]benzoxa(or thia)zinc-2-carboxylic acid lower alkyl esters, derivatives thereof, process for their preparation, pharmaceutical compositions thereof and methods for using the compounds. The compounds of this invention are useful in the treatment of anaphylactic reactions and allergic conditions in a mammal.

11 Claims, No Drawings

1-OXO-5H-PYRIMIDO[2,1-C]BENZOXAZINE-2-CARBOXYLIC ACID ESTERS

This is a division of application Ser. No. 65,790, filed Aug. 13, 1979, which on Mar. 3, 1981, became U.S. Pat. No. 4,254,118.

BACKGROUND OF THE INVENTION (a) Field of the Invention

This invention relates to novel 1-oxo-5H-pyrimido[2,1-c][1,4]benzoxa(or thia)zine-2-carboxylic acid lower alkyl esters, to derivatives thereof, to therapeutically acceptable basic addition salts thereof, to process for the preparation and to pharmaceutical compositions. The compounds of this invention are useful in the treatment of anaphylactic reactions and allergic conditions in mammals.

(b) Description of the Prior Art

A search of the chemical literature indicates that the compounds of this invention represent a novel tricyclic ring system. A number of related tricyclic compounds are described in the following reports: S. B. Kadin, U.S. Pat. No. 4,017,625, issued May 24, 1976; S. B. Kadin, U.S. Pat. No. 4,066,766, issued Jan. 3, 1978; and S. B. Kadin and P. F. Moore, U.S. Pat. No. 4,031,217, issued June 21, 1977. These references disclose compounds which, like the compounds of this invention, are tricyclic; however, the tricyclic compounds in these references differ by being "carba" analogs.

SUMMARY OF THE INVENTION

The compounds of this invention are represented by formula I

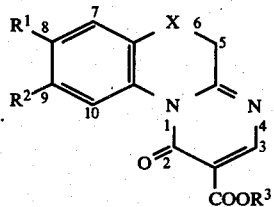

in which $R^1$ is hydrogen, lower alkyl, halo, lower alkoxycarbonyl, carboxy, nitro or trifluoromethyl; $R^2$ is hydrogen, lower alkyl, halo, nitro or trifluoromethyl; $R^3$ is lower alkyl, and X is oxygen or sulfur.

A preferred group of compounds is represented by formula I in which $R^1$ is hydrogen, lower alkyl, halo, lower alkoxycarbonyl or carboxy; $R^2$ is hydrogen, lower alkyl or halo; $R^3$ is lower alkyl; and X is oxygen or sulfur.

A more preferred group of compounds is represented by formula I in which $R^1$ is hydrogen or lower alkyl; $R^2$ is hydrogen or halo; $R^3$ is lower alkyl; and X is oxygen or sulfur.

The therapeutically acceptable basic addition salts of the compounds of formula I in which $R^1$ is carboxy and $R^2$, $R^3$ and X are as defined herein are also included within the scope of this invention.

The compounds of formula I are prepared by the following process:

condensing a compound of formula II

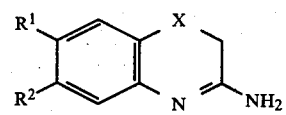

in which $R^1$ is hydrogen, lower alkyl, halo, lower alkoxycarbonyl, nitro or trifluoromethyl; $R^2$ is hydrogen, lower alkyl, halo, nitro or trifluoromethyl; and X is oxygen or sulfur with a compound of formula III

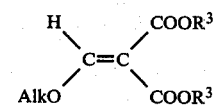

in which $R^3$ and Alk each is lower alkyl to obtain the corresponding compound of formula IV

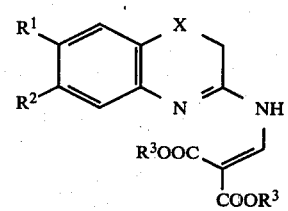

in which $R^1$, $R^2$, $R^3$ and X are as defined immediately above, and cyclizing said compound of formula IV to obtain said compound of formula I in which $R^1$, $R^2$, $R^3$ and X are as defined immediately above; if desired, hydrolyzing the compound of formula I in which $R^1$ is lower alkoxycarbonyl and $R^2$, $R^3$ and X are as defined herein with aqueous potassium or sodium hydroxide to obtain the corresponding compound of formula I in which $R^1$ is carboxy; and if desired, reacting the last-named compound of formula I with a therapeutically acceptable base to obtain the corresponding therapeutically acceptable basic addition salt of the compound of formula I in which $R^1$ is carboxy.

The compounds of this invention are useful for preventing or treating anaphylactic reactions or allergic conditions in a mammal by administering to the mammal an effective anaphylactic alleviating or allergic alleviating amount of a compound of formula I or a therapeutically acceptable basic addition salt of the compound of formula I in which $R^1$ is carboxy and $R^2$, $R^3$ and X are as defined herein.

The compounds of this invention form a pharmaceutical composition which comprises a compound of formula I, or a therapeutically acceptable basic addition salt of the compound of formula I in which $R^1$ is carboxy and $R^2$, $R^3$ and X are as defined herein, and a pharmaceutically acceptable carrier.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl propyl, isopropyl, butyl, isobutyl, pentyl, hexyl and the like. 1,1-Dimethylethyl used herein is also known as tert-butyl.

The term "halo" as used herein means halogens and includes fluorine, chlorine, bromine and iodine, unless stated otherwise.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkanol" as used herein means both straight and branched chain alkanols containing from one to four carbon atoms and includes methanol, ethanol, isopropanol, butanol, t-butanol and the like.

The term "strong proton acceptor" as used herein means a strong base of the type exemplified by: sodium ethoxide, potassium methoxide, t-butyl lithium, sodium hydride and the like.

The acidic compounds of formula I, in which $R^1$ is carboxy, form salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as tetraalkyl (for example tetramethyl), alkylalkanol (for example methyltriethanol and trimethylmonoethanol) and cyclic ammonium salts, for example the N-methylpyridinium, N-methyl-N-(2-hydroxyethyl)-morpholinium, N,N-dimethylmorpholinium, N-methyl-N-2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts, wherein the cation is quaternary ammonium, are produced by mixing the acid of formula I with an equivalent amount of the corresponding quaternary ammonium hydroxide in water solution, followed by evaporation of the water.

ANTI-ALLERGIC ACTIVITY

The compounds of this invention of formula I or a therapeutically acceptable basic addition salt of a compound of formula I in which R is carboxy are useful in the prevention or treatment of allergic reactions in a mammal.

More specifically, the compounds of this invention are useful for the prophylactic treatment as well as for the management of anaphylactic reactions and atopic allergic manifestations, for example, bronchial asthma, hay fever, allergic rhinitis, allergic conjunctivitis, food allergies, urticaria and the like, in a sensitized mammal.

The prevention or treatment of allergic reactions in a mammal by administration of a compound of formula I is demonstrated by using known anti-allergic tests in an appropriate animal model.

In one such test, the compounds of this invention are effective anti-allergic agents when tested using the passive cutaneous anaphylaxis (PCA) method, described by I. Mota, Immunology, 7, 681 (1964). The anti-allergic activity of a given compound is measured in rats by its ability to inhibit the increase in vascular permeability at the site of injection of rat immunoglobulin E (IgE) followed by i.v. administration of the specific antigen. Evans blue is injected i.v. at the same time as the specific antigen, and the size of the wheal or of the area infiltrated with Evans blue is measured and compared with that of untreated controls. By using this test, the following representative compound of formula I, 1-oxo-5H-pyrimido[2,1-c][1,4]benzoxazine-2-carboxylic acid ethyl ester (described in Example 6), at an oral dose of 25 mg per kg of body weight, is an effective anti-allergic agent in rats reducing the wheal size by 42% at 30 minutes after dosing.

In another test for useful anti-allergic activity, the compounds of formula I are tested using the passive paw anaphylaxis (PPA) method, described by R. R. Martel and J. Klicius, Int. Archs. Allergy Appl. Immun., 54, 205 (1977). In this method reaginic antibody-induced hypersenstivity is produced in the rat hindpaw. Increased vacular permeability is determined by measuring the increase in paw volume. An effective anti-allergic drug inhibits the increase in paw volume when compared to untreated reaginic hypersensitive controls. In this test, the following illustrative compounds of formula I are effective anti-allergic agents:

1-oxo-5H-pyrimido[2,1-c][1,4]benzoxazine-2-carboxylic acid ethyl ester (described in Example 6) at an oral dose of 10 mg/kg of body weight causes at 28% inhibition at 30 minutes of the increase in paw volume, 9-chloro-1-oxo-5H-pyrimido[2,1-c][1,4]benzoxazine-2-carboxylic acid ethyl ester (described in Example 6) at an intraperitoneal dose of 30 mg per kg of body weight causes a 50% inhibition at 15 minutes of the increase in paw volume, 1-oxo-5H-pyrimido-[2,1-c][1,4]benzothiazine-2-carboxylic acid ethyl ester (described in Example 6) at an intraperitoneal dose of 30 mg per kg of body weight causes a 33% inhibition at 30 min of the increase in paw volume and 8-methyl-1-oxo-5H-pyrimido[2,1-c][1,4]benzoxazine-2-carboxylic acid ethyl ester (described in Example 6) at an intraperitoneal dose of 30 mg per kg of body weight causes at 42% inhibition at 15 minutes of the increase in paw volume.

When the compounds of formula I of this invention are used for suppressing allergic manifestations of anaphylactic reactions and atopic hypersensitivity in a mammal, they are used alone or in combination with pharmacologically acceptable carriers, the proportion of which is determined by the solubility and the chemical nature of the compound, chosen route of administration and standard biological practice.

For example, they are administered orally in solid form i.e. capsule or tablet. They can also be administered orally in the form of suspensions or solutions or they may be injected parenterally. They can be administered parenterally by the nasal route, for instance, as drops or aerosol; or by inhalation from an aerosol.

In addition, the compounds of this invention can be administered in conjunction with common anti-allergic agents, for example, known compounds effecting antihistaminic, analgesic, central nervous system depressant, anti-hypertensive, immunosupressive, anti-bradykinin, anti-serotonin or endocrinological responses.

The tablet compositions for oral administration contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I for oral administration contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions for oral adminsitration can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or ethyl alcohol. These compositions can also contain a sweetening agent, flavoring agent and antioxidant.

For administration to a mammal by parenteral injection, it is preferred to use the compounds of formula I in solution in a sterile aqueous vehicle which may also contain other solutes, such as buffers or preservatives, as well as sufficient quantities of pharmaceutically acceptable salts or of glucose to make the solution isotonic.

The compounds of formula I can also be administered as nasal powders or insufflations. For such purpose, the compounds are administered in finely divided solid form together with a pharmaceutically acceptable solid carrier, for example, a finely divided polyethylene glycol (e.g. "Carbowax 1540") of finely divided lactose. Such compositions may also contain other excipients in finely divided solid form.

For administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of formula I as anti-allergic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, an effective anti-allergic amount of a compound of formula I usually ranges from about 0.1 mg to about 500 mg per kg of body weight per day in single or divided dose, although as aforementioned, variations will occur. However, a dosage level that is in the range from about 0.5 mg to about 200 mg per kg of body weight per day in single or divided dose is employed most desirably in order to achieve effective results.

PROCESS

For the preparation of the compounds of formula I, the preferred starting materials are the compounds of formula II in which $R^1$ is hydrogen, lower alkyl, halo, lower alkoxycarbonyl, nitro or trifluoromethyl; $R^2$ is hydrogen, lower alkyl, halo, nitro or trifluoromethyl and X is oxygen or sulfur. Reaction Scheme I illustrates a preferred method for the preparation of the starting materials of formula II.

Reaction Scheme 1

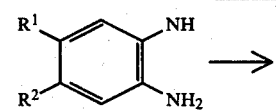

(V)

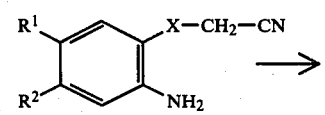

(VI)

-continued
Reaction Scheme 1

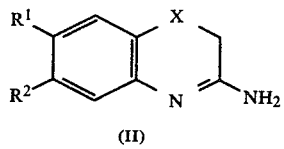

(II)

The sequence of reactions illustrated in Reaction Scheme I is essentially described by M. Mazharuddin and G. Thyagarajan in Chem. and Ind., 178 (1971) for the preparation of the compound of formula II in which $R^1$ and $R^2$ are hydrogen and X is oxygen. For the preparation of the compounds of formula II, the phenol or thiophenol derivatives of formula V either are known and commercially available or are prepared by conventional methods described in the chemical literature. Condensation of the compound of formula V in which $R^1$ is hydrogen, lower alkyl, halo, lower alkoxycarbonyl, nitro or trifluoromethyl; and $R^2$ and X are as defined herein with 1.1 to 1.5 molar equivalents of chloroacetonitrile and potassium carbonate in acetone at 20° to 60° C. for four to ten days affords the corresponding compound of formula VI in which $R^1$, $R^2$ and X are as defined immediately above. In turn, the compound of formula VI is treated with five to eight molar equivalents of sodium methoxide in methanol at 15° to 30° C. for one-half to five hours to give the corresponding compound of formula II in which $R^1$, $R^2$ and X are as defined immediately above.

Reaction Scheme 2 illustrates the conversion of the compound of formula II to the compounds of formula I.

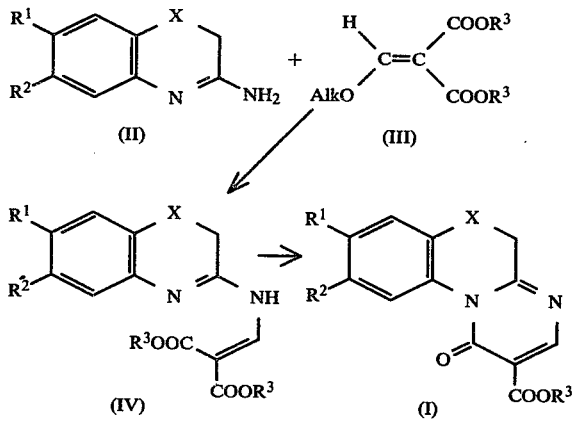

Reaction Scheme 2

In the first step, the compound of formula II in which $R^1$, $R^2$ and X are as defined immediately above is condensed with 0.9 to 1.2 molar equivalents of the compound of formula III in which $R^3$ and Alk each is lower alkyl at 20° to 80° C. for 5 to 30 hours to obtain the corresponding compound of formula IV in which $R^1$ is hydrogen, lower alkyl, halo, lower alkoxycarbonyl, nitro or trifluoromethyl; $R^2$ is hydrogen, lower alkyl, halo, nitro or trifluoromethyl; $R^3$ is lower alkyl; and X is oxygen or sulfur. A suitable solvent for the condensation can be selected from a lower alkanol, preferably ethanol.

The latter compound of formula IV is cyclized to obtain the corresponding compound of formula I in which $R^1$, $R^2$, $R^3$ and X are as defined immediately above. This cyclization is achieved by reacting the compound of formula IV with an excess of polyphosphoric acid (for example, 1.0 to 2.0 grams per millimole of the compound of formula IV) at 75° to 130° C. for one-half to five hours. In the case of the compound of formula IV in which $R^1$ is hydrogen, lower alkyl, halo, nitro or trifluoromethyl and $R^2$, $R^3$ and X are as defined immediately above, cyclization is also effected by reacting the latter compound of formula IV with 10 to 40 molar equivalents of a strong proton acceptor, preferably potassium or sodium lower alkoxide, at 10° to 40° C. for one-half to five hours to obtain the corresponding compound of formula I in which $R^1$, $R^2$, $R^3$ and X are as defined immediately above. Suitable inert solvents for this cyclization can be selected from a lower alkanol, preferably methanol or ethanol. Furthermore, this cyclization should be performed under anhydrous conditions, i.e. with dry solvents and reagents, and exclusion of atmospheric moisture, in order to obtain optimum yields.

If desired, the compound of formula I in which $R^1$, $R^2$ and $R^3$ are as defined immediately above and X is sulfur is oxidized with a suitable oxidizing agent, preferably with 1.0 to 1.2 molar equivalents of 3-chloroperbenzoic acid at 20° to 30° C. for 20 to 30 hours, to obtain the corresponding sulfinyl compound. Suitable inert solvents for use with 3-chloroperbenzoic acid as oxidizing agent can be selected from a halogenated hydrocarbon, preferably methylene chloride or chloroform.

Alkaline hydrolysis of the compound of formula I in which $R^1$ is lower alkoxycarbonyl and $R^2$, $R^3$ and X are as defined herein, preferably with 10 to 100 molar equivalents of aqueous potassium or sodium hydroxide at 0° to 30° C. for 15 minutes to 5 hours, followed by acidification of the solution gives the corresponding compound of formula I in which $R^1$ is carboxy and $R^2$, $R^3$ and X are as defined herein. For this hydrolysis, a water miscible organic solvent, preferably methanol or ethanol, is usually required to disolve the starting material of formula I in the aqueous alkaline solution.

The following examples illustrate further this invention.

EXAMPLE 1

2-Amino-4-(1,1-dimethylethyl)phenol[V; $R^1$=H, $R^2$=C(CH$_3$)$_3$ and X=O]

4-(1,1-Dimethylethyl)phenol (30.0 g, 200 mmol) was added to a vigorously stirred solution of sodium hydroxide (24.5 g, 500 mmol) in water (540 ml). The mixture was heated over a steambath to dissolve the phenol and the solution was cooled to 10° C. Benzenediazonium chloride [prepared from aniline (18.6 g, 200 mmol), crushed ice (250 g), concentrated hydrochloric acid (58 ml) and sodium nitrite (14.3 g, 200 mmol)] was added to the stirred suspension. After the addition (40 min), the precipitate was collected and air dried to afford the azo derivative as an orange powder (49.3 g), mp 65°–66° C.

A part of this material (48.0 g, 189 mmol) was suspended in aqueous sodium hydroxide (69.5 g in 400 ml of water); the mixture was heated at 75° C. while sodium dithionite (87 g) was added in portions over a period of 1 hr. At the end of the addition, the red color turned to a straw like tint. The hot solution was mixed with charcoal and filtered through a cake of diatomaceous earth. The solution was acidified with 6 N hydrochloric acid to pH 5–6 and upon cooling, a tan precipitate deposited. The material was collected and air-dried to give a tan powder of the title compound (19.3 g): mp 158°–159√ C., and nmr(DMSO-d6)δ 1.25 (9H, s), 4.25 (2H, s), 6.5 (3H, m) and 8.0 (1H, s).

EXAMPLE 2

2-Cyanomethoxy-5-(1,1-dimethylethyl)benzenamine [VI; $R^1$=H, $R^2$=C(CH$_3$)$_3$ and X=O]

2-Amino-4-(1,1-dimethylethyl)phenol (90.0 g, 546 mol, described in Example 1) was dissolved in acetone (900 ml) and refluxed in the presence of anhydrous potassium carbonate (81.0 g, 534 mmol) and chloroacetonitrile (40.5 g, 535 mmol). After stirring 2 days under these conditions and allowing to stand an additional day at room temperature, the mixture was treated with more potassium carbonate (15.0 g) and chloroacetonitrile (10 g) under the same conditions. The mixture was mixed with charcoal and filtered through diatomaceous earth. The filtrate was evaporated to afford a residue which, when dissolved in hexane containing a small amount of ethyl acetate, afforded tan crystals of the title compound; Anal. Calcd for $C_{12}H_{16}N_2O$: C, 70.56% H, 7.90% N, 13.72% and Found: C, 70.60% H, 8.00% N, 13.85%); ir (CHCl$_3$) 3460, 3380, 2240, 1620, 1515 and 1166 cm$^{-1}$; av max (CH$_3$OH) 288 ($\epsilon$3,175) and 235 nm ($\epsilon$7,660); and nmr(CDCl$_3$) δ1.3 (9H, s), 3.7 (2H, s), 4.7 (2H, s) and 6.75 (3H, s).

In a similar manner, but replacing 2-amino-4-(1,1-dimethylethyl)phenol with an equivalent amount of 2-aminophenol, 2-amino-4-chlorophenol, 2-amino-5-methylphenol or 2-aminothiophenol, the following compounds of formula VI were obtained, respectively: 2-cyanomethoxybenzenamine (described by M. Mazharuddin and G. Thyagarajan, cited above); mp 102° C., ir(nujol) 3,460, 3,370 and 2,260 cm$^{-1}$; and nmr(CDCl$_3$) δ3,85 (2H, s), 4.73 (2H, s) and 6.85 (4H, m); 5-chloro-2-cyanomethoxybenzenamine: mp 68°–70° C.; ir (CHCl$_3$) 3,490, 3,390 and 1,188 cm$^{-1}$ and nmr(CDCl$_3$) δ3.9 (2H, s), 4.7 (2H, s) and 6.7 (3H, m); 2-cyanomethoxy-4-methylbenzenamine: mp 37°–89° C.; Anal. Calcd for $C_9H_{10}N_2O$: C, 66.65% H, 6.22% N, 17.27% and Found: C, 66.90% H, 6.13% H, 18.06%; ir(CHCl$_3$) 3,450 and 3,380 cm$^{-1}$; uv max(CH$_3$OH) 291 ($\epsilon$2,630) and 237 nm($\epsilon$8,760); and nmr(CDCl$_3$) δ2.25 (3H, s), 3.62 (2H, s), 4.73 (2H, s) and 6.7 (3H, m); and 2-[(cyanomethyl)thio]-benzenamine: ir(CHCl$_3$) 3,463, 3.368, 2.246 and 1,605 cm$^{-1}$; uv max(CH$_3$OH) 307 ($\epsilon$3,300) and 237 nm ($\epsilon$7,275) and nmr(CDCl$_3$) δ3.47 (2H, s), 4.37 (2H, s), 6.7 (2H,m), 7.25 (1H, m) and 7.48 (1H, m).

EXAMPLE 3

3-Amino-6-(1,1-dimethylethyl)-2H-1,4-benzoxazine [H; $R^1$=H, $R^2$=C(CH$_3$)$_3$ and X=O]

2-Cyanomethoxy-5-(1,1-dimethylethyl)benzenamine (4,0 g, 19.6 mmol, described in Example 2) was dissolved in methanol (80 ml) containing 5.2 meq. of freshly prepared sodium methoxide. The mixture was stirred at 20° C. for 1 hr and evaporated. Water (100 ml) was added and the solution was extracted with methylene chloride. The organic was dried and evaporated, and the residue was crystallized from ethyl acetate-hexane to give the title compound (1.46 g, 37%): mp 155°–156° C.; Anal. Calcd for $C_{12}H_{16}N_2O$: C, 70.56% H, 7.90% N, 13.72% and Found: C 70.77% H, 7.96% N, 13.96%; ir(CHCl$_3$) 3504, 3480, 3400, 1643, 1598 and 1574 cm$^{-1}$; uv max(CH$_3$OH) 296 ($\epsilon$7,860), 281 ($\epsilon$9,550), 274 ($\epsilon$9,570) and 221 nm($\epsilon$28,560); and nmr(CDCl$_3$)δ1.32 (9H, s), 4.43 (2H, s) and 6.60–7.10 (3H, m).

In a similar manner, but replacing 2-cyanomethoxy-5-(1,1-dimethylethyl)benzenamine with an equivalent amount of another compound of formula VI, described in Example 2, the following compounds of formula II were obtained, respectively: 3-amino-2H-1,4-benzoxazine (described by M. Mazharudin and G. Thyagarajan, cited above): mp 117°–119° C. and nmr(CDCl$_3$)δ4.4 (2H, s), 5.6 (2H, s) and 6.9 (4H, m); 3-amino-6-chloro-2H-1,4-benzoxazine: mp 173°–175° C.; Anal. Calcd for $C_8H_7$-ClN$_2$O: C, 52.61% H, 3.86% N, 15.34% and Found: C, 52.56% H, 3.85% N, 14.86%; and nmr(CDCl$_3$)δ4.45 (2H, s), 6.85 (3H, m) and 7.05 (2H, s); 3-amino-7-methyl-2H-1,4-benzoxazine: mp 167°–170° C.; Anal. Calcd for $C_9H_{10}N_2O$: C, 66.65% H, 6.22% N, 17.27% and Found: C, 66.63% H, 6.14% N, 16.88%; ir(CHCl$_3$) 3,500, 3,400, 3,000 and 1650 cm$^{-1}$; uv max(CH$_3$OH) 282($\epsilon$10,550) and 218 nm($\epsilon$23,510); and nmr(CDCl$_3$) δ2.3 (3H, s), 4.45 (2H, s), 5.25 (2H, s) and 6.8 (3H, m); and 3-amino-2H-1,4-benzothiazine: mp 162°–164° C.; Anal. Calcd for $C_8H_8N_2S$: C, 58.53% H, 4.91% N, 17.07% and Found: C, 58.48% H, 4.86%, N, 16.99%; ir(nujol) 3,430, 3,000 and 1,643 cm$^{-1}$; uv max(CH$_3$OH) 295($\epsilon$5,100) and 254 nm(δ19,860) and nmr(DMSO-d$_6$) δ 3.15 (2H, s), 6.9 (4H, m) and 6.7 (2H, s).

EXAMPLE 4

3-Amino-7-ethoxycarbonyl-2H, 1,4-benzoxazine [H: $R^1$=COOEt, $R^2$=H and X=O]

3-Hydroxy-4-nitrobenzoic acid (20.0 g, 199 mmol) in ethanol (250 mg) was refluxed for 6 hr in the presence of dry hydrogen chloride (5 g). The solvent was evaporated and the residue was dissolved in methylene chloride. The solution was washed with sodium bicarbonate until the unreacted material was removed as a precipitate. The organic fraction was finally washed with brine, dried over magnesium sulfate to give a brown solid of 3-hydroxy-4-nitrobenzoic acid ethyl ester (17.1 g): mp 80°–81° C. (crystallized from diethyl ether-hexane); Anal. Calcd for $C_9H_9NO_5$: C, 51.19% H, 4.30% N, 6.6% and Found: C, 51.23% H, 4.30% N, 6.79%; ir(CHCl$_3$) 3,260, 1,720, 1,535 and 1,320 cm$^{-1}$; and nmr(CDCl$_3$) δ1.35 (3H, t), 4.3 (2H, q), 7.7 (3H, m) and 10.4 (1H, s).

The latter compound (8.0 g) was hydrogenated over 10% palladium on carbon (0.80 g) in ethanol (100 ml) and filtered. The filtrate was evaporate and the residue was crystalized from diethyl ether-hexane to obtain 4-amino-3-hydroxybenzoic acid ethyl ester (4.65 g): mp 96.5°–97.5° C.; Anal. Calcd for $C_9H_{11}NO_3$: C, 59.66% H, 6.12% N, 7.73% and Found: C, 59.68% H, 6.24% N, 7.64%; ir(CHCl$_3$) 3,580, 3,370 and 1,685 cm$^{-1}$; uv max(CH$_3$OH) 309 ($\epsilon$15,040), 282 ($\epsilon$10,980) and 230 nm($\epsilon$12,410): and nmr(CDCl$_3$) δ1.3 (3H, t), 4.25 (2H, q), 4.8 (3H, s) and 6.5–7.6 (3H, m).

The latter compound (5.43 g) was refluxed with chloroacetonitrile (2.34 g, 31.2 mmol) in acetone (50 ml) in the presence of anhydrous potassium carbonate (4.14 g, 30 mmol). After 24 hr, the insoluble salts were removed by filtration and filtrate was evaporated to afford a solid residue. Recrystallization of the bulk of material from ethyl acetate-hexane gave a brown powder of 4-amino-3-cyanomethoxybenzoic acid ethyl ester (5.17 g): mp 140°–142.5° C.; Anal. Calcd for $C_{11}H_{12}N_2O_3$: C, 59.99% H, 5.49% N, 12.72% and Found: C, 59.85% H, 5.67% N, 12.65%; ir(CHCl$_3$) 3,480, 3,360, 3,200, 2,260, 1,675 and 1,260 cm$^{-1}$; uv max(CH$_3$OH) 299 ($\epsilon$17,220) and 225 nm($\epsilon$11,670); and nmr(CDCl$_3$) $\delta$1.35 (3H, t), 4.25 (2H, s), 4.3 (2H, q), 4.8 (2H, s) and 7.1 (3H, m).

A solution of the latter compound (2.20 g) and sodium ethoxide (2.5 equivalents) in ethanol (20 ml) was refluxed for 3 hr. The precipitate was collected and dried to give the title compound (1.92 g): mp 232°–233° C.; Anal. Calcd for C$_{11}$H$_{12}$N$_2$O$_3$: C, 59.99% H, 5.49% N, 12.72% and Found: C, 60.27% H, 5.60% N, 12.80%; ir(nujol) 3,380, 2,950, 1,673, 1,684, 1,563 and 1,290 cm$^{-1}$; uv max(CH$_3$OH) 318 ($\epsilon$19,025), 294 ($\epsilon$17,295) and 228 nm($\epsilon$19,390); and nmr(DMSO-d$_6$) $\delta$1.3 (3H, t), 4.2 (2H, q), 4.45 (2H, s), 7.15 (2H, s) and 6.8–7.5 (3H, m).

EXAMPLE 5

2-[[N-[6-(1,1-Dimethylethyl)-2H-1,4-benzoxazin-3-yl]amino]methylene]-propanedioic acid, diethyl ester [IV; R$^1$=H, R$^2$=C(CH$_3$)$_3$, R$^3$=Et and X=O]

A solution of 3-amino-6-(1,1-dimethylethyl)-2H-1,4-benzoxazine (1.0 g, 4.9 mmol, described in Example 3) and 2-(ethoxymethylene)-propanedioic acid diethyl ester (1.0 g, 4.63 mmol) in ethanol (10 ml) ws stirred for 18 hr at 20° to 22° C. and evaporated. The residue was crystallized from hexane to give the title compound (1.70 g): mp 92° C.; Anal. Calcd for C$_{20}$H$_{26}$N$_2$O$_5$: C, 64.15% H, 7.00% N, 7.48% and Found: C, 64.55% H, 7.12% N, 7.42%; ir(CHCl$_3$)3,260 1,704 and 1,656 cm$^{-1}$; uv max(CH$_3$OH) 345 ($\epsilon$20,655) and 264 nm($\epsilon$11,100); nm$\epsilon$(CDCl$_3$) $\delta$1.30 (9H, s), 1.33 (6H, t), 4.20 (2H, q), 4.23 (2H, q), 4.55 (2H, s), 6.60–7.30 (3H, m) and 8.82 (1H, d).

In a similar manner, but replacing 3-amino-6-(1,1-dimethylethyl)-2H-1,4-benzoxazine with an equivalent amount of another compound of formula II described in Example 3 or Example 4, the following compounds of formula IV were obtained, respectively: 2-[[N-(2H-1,4-benzoxazin-3-yl)amino]methylene]propanedioic acid, diethyl ester: mp 102°–103° C. (crystallized from 2-propanol-hexane); ir(CHCl$_3$) 3,280, 1,705 and 1,656 cm$^{-1}$; uv max(CH$_3$OH) 342 ($\epsilon$24,960) and 260 nm($\epsilon$9,930); nmr(CDCl$_3$) $\delta$1.3 (6H, t), 4.17 (4H, q), 4.35 (2H, s), 6.75 (4H, m), 8.50 (1H, d) and 10.10 (1H, d); and Anal. Calcd for C$_{16}$H$_{18}$N$_2$O$_5$: C, 60.37% H, 5.70% N, 8.80% and Found: C, 60.31% H, 5.62% N, 8.69%; 2-[[N-(6-chloro-2H-1,4-benzoxazin-3-yl)amino]methylene]propanedioic acid, diethyl ester: mp 117.5°–118° C. (crystallized from diethyl ether-petroleum ether); ir(CHCl$_3$) 3,260, 1715 and 1,660 cm$^{-1}$; uv max(CH$_3$OH) 344 ($\epsilon$23,710) and 264 nm($\epsilon$11,055); nmr(CDCl$_3$) $\delta$1.45 (6H, t), 4.3 (4H, q), 4.65 (2H, s), 7.0 (3H, m), 8.85 (1H, d) and 10.6 (1H, d); and Anal. Calcd for C$_{16}$H$_{17}$ClN$_2$O$_5$:C, 54.57% H, 4.85% N, 7.94% and Found: C, 54.78% H, 4.71% N, 7.70%; 2-[[N-(7-methyl-2H-1,4-benzoxazin-3-yl)amino]methylene]-propanedioic acid, diethyl ester: mp 99°–101° C. (crystallized from ethyl acetate-hexane); ir(CHCl$_3$) 3,260, 1,710 and 1,660 cm$^{-1}$; uv max(CH$_3$OH) 342 ($\epsilon$22,365) and 263 nm($\epsilon$10,600); nmr(CDCl$_3$) $\epsilon$1.35 (6H, t), 2.3(3H, s), 4.25 (4H, q), 4.6 (2H, s), 6.95 (3H, m), 8.85 (1H, d) and 10.4 (1H, d); and Anal. Calcd for C$_{17}$H$_{20}$N$_2$O$_5$: C, 61.43% H, 6.03% N, 8.43% and Found: C, 61.67% H, 6.07% N, 8.29%; 2[[N-(2H, 1,4-benzothiazin-3-yl)amino]methylene]-propanedioic acid diethyl ester: mp 105°–106° C. (crystallized from ethyl acetate-hexane); ir(CHCl$_3$) 3,270, 1710 and 1,660 cm$^{-1}$; uv max(CH$_3$OH) 350 ($\epsilon$18,855), 330 ($\epsilon$19,660), 279 ($\epsilon$15,950), 227 ($\epsilon$15,410) and 214 nm($\epsilon$19,390); nmr(CDCl$_3$) $\epsilon$1.4 (6H, t), 3.33 (2H, s), 4.3 (4H, q), 7.2 (4H, m), 8.98 (1H, d) and 10.5 (1H, d); and Anal. Calcd for C$_{16}$H$_{18}$N$_2$SO$_4$: C, 57.48% H, 5.43% N, 8.38% and Found: C, 57.60% H, 5.43% N, 3.26% and 2-[[N-(7-ethoxycarbonyl-2H-1,4-benzoxazin-3-yl)amino]methylene]propanedioic acid, diethyl ester: mp 152°–154° (crystallized from ethanol); ir(CHCl$_3$) 3,250, 1,705, 1,660, 1,615, 1,578 and 1,095 cm$^{-1}$; uv max(CH$_3$OH) 351($\epsilon$32,939) and 263 nm($\epsilon$8,395); nmr(CDCl$_3$) 1.4 (9H, t), 4.3 (6H, q), 7.4 (3H, m), 8.86 (1H, d) and 10.5 (1H, d); and Anal. Calcd. for C$_{19}$H$_{22}$N$_2$O$_7$: C, 58.45% N, 7.18% and Found: C, 58.57% H, 5.79% N, 7.47%.

Similarly, by replacing 3-amino-6-(1,1-dimethylethyl)-2H-1,4-benzoxazine with an equivalent amount of 3-amino-7-bromo-2H-1,4-benzoxazine, 3-amino-8-ethyl-7-nitro-2H-1,4-benzoxazine, 3-amino-7-trifluoromethyl-2H-1,4-benzoxazine, 3-amino-6-nitro-2H-1,4-benzoxazine, 3-amino-6-trifluoromethyl-2H-1,4-benzoxazine, 3-amino-6-hexyl-7-propyl-2H-1,4-benzoxazine, 3-amino-7-butyl-6-iodo-2H-1,4-benzothiazine or 3-amino-7-iodo-2H-1,4-benzoxazine, the following compounds of formula IV are obtained, respectively: 2-[[N-(7-bromo-2H-1,4-benzoxazin-3-yl)amino]methylene]-propanedioic acid, diethyl ester, 2-[[N-(6-ethyl-7-nitro-2H-1,4-benzoxazin-3-yl)-amino]methylene]-propanedioic acid, diethyl ester, 2-[[N-(7-trifluoromethyl-2H-1,4-benzoxazin-3-yl)amino]methylene]propanedioic acid, diethyl ester, 2-[[N-(6-nitro-2H-1,4-benzoxazin-3-yl)amino]methylene]-propanedioic acid, diethyl ester, 2-[[N-(6-trifluoromethyl-2H-1,4-benzoxazin-3-yl)amino]methylene]-propanedioic acid, diethyl ester, 2-[[N-(6-hexyl-7-propyl-2H-1,4-benzoxazin-3-yl)amino]methylene]propanedioic acid, diethyl ester, 2-[[N-(7-butyl-6-iodo-2H-1,4-benzothiazin-3-yl)amino]methylene]-propanedioic acid, diethyl ester and 2-[[N-(7-iodo-2H-1,4-benzoxazin-3-yl)amino]methylene]-propanedioic acid, diethyl ester.

EXAMPLE 6

9-(1,1-Dimethylethyl)-1-oxo-5H-pyrimido[2,1-c][1,4]benzoxaxine-2-carboxylic Acid, Ethyl Ester [I: R$^1$=H, R$^2$=C(CH$_3$)$_3$; R$^3$=Et and X=O]

2-[[N-[6-(1,1-Dimethylethyl)-2H-1,4-benzoxazin-3-yl]amino]methylene]-propanedioic acid, diethyl ester (6.6 g, 17.6 mmol, described in Example 5), was dissolved in ethanol (120 ml) containing 30 meq. of freshly prepared sodium ethoxide. After stirring at 20° C. for 2 hr, the dark solution was poured in water (800 ml) containing 5 ml of 2N hydrochloric acid. The suspension was extracted with ethyl acetate and the combined extracts were washed with water, brine, dried over magnesium sulfate and evaporated to afford an oily residue which solidified on standing. Recrystallization of the residue from ethyl acetate gave the title compound (2.0 g): mp 153°–154° C.; ir(CHCl$_3$) 1,740, 1,710, 1,610 and 1,586 cm$^{-1}$; uv max(CH$_3$OH) 332 ($\epsilon$8,470) and 260 nm($\epsilon$4,370); nmr(CDCl$_3$) $\delta$1.32 (9H, s), 1.38 (3H, t), 4.34 (2H, q), 4.85 (2H, s), 6.97 (1H, d), 7.25 (1H, two doublets), 8.55 (1H, d) and 8.43 (1H, s); Anal. Calcd for C$_{18}$H$_{20}$N$_2$O$_4$: C, 65.84% H, 6.14% N, 8.53% and Found: C, 65.96% H, 6.14% N, 8.56%.

In a similar manner, but replacing 2-[1N-[6-(1,1-dimethylethyl)-2H-1,4-benzoxazin-3-yl]amino]methylene]-propanedioic acid, diethyl ester with an equivalent amount of a following compound of formula IV described in Example 5: 2-[[N-(2H-1,4-benzoxazin-3- yl)amino]methylene]propanedioic acid, diethyl ester, 2-[[N-(6-chloro-2H-1,4-benzoxazin-3-yl)amino]methylene]-propanedioic acid, diethyl ester, 2-[[N-(7-methyl-2H, 1,4-benzoxazin-3-yl)amino]methylene]-propanedioic acid, diethyl ester, or 2[[N-(2H-1,4-benzothiazin-3-yl)amino]methylene]-propanedioic acid, diethyl ester, the following compounds of formula I were obtained, respectively: 1-oxo-5H-pyrimido[2,1-c][1,4]benzoxazin-2-carboxylic acid, ethyl ester: mp 101°–102° C. (crystallized from ethyl acetate-hexane); ir(CHCl$_3$) 1,745 and 1,715 cm$^{-1}$; uv max(CH$_3$OH) 330 ($\epsilon$8,250); nmr(CDCl$_3$) δ1.45 (3H, t), 4.9 (2H, q), 4.95 (2H, s), 7.2 (3H, m) and 8.55 (2H, m); and Anal. Calcd for C$_{14}$H$_{12}$N$_2$O$_4$: C, 61.76% H, 4.44% N, 10.29% and Found: C, 61.72% H, 4.39% N, 10.16%: 9-chloro-1-oxo-5H-pyrimido[2,1-c][1,4-benzoxazine-2-carboxylic acid, ethyl ester: mp 115°–116° C. (crystallized from benzene-hexane); ir(CHCl$_3$) 1,746 and 1,716 cm$^{-1}$; uv max(CH$_3$OH) 329 nm($\epsilon$8,205); nmr(CDCl$_3$) δ1.4 (3H, t), 4.36 (2H, q), 4.9 (2H, s), 7.2 (2H, m) and 8.55 (2H, m); and Anal. Calcd for C$_{14}$H$_{11}$ClN$_2$O$_4$: C, 54.82% H, 3.62% N, 9.14% and Found: C, 54.80% H, 3.53% N, 9.17%; 8-methyl-1-oxo-5H-pyrimido[2,1-c][1,4]benzoxazine-2-carboxylic acid, ethyl ester: mp 110.5°–111.5° C. (crystalized from ethyl acetatehexane); ir(CHCl$_3$) 1,745 and 1,710 cm$^{-1}$; uv max(CH$_3$OH) 335 (9,320) and 253 nm($\epsilon$4,295); nmr(CDCl$_3$) δ1.4 (3H, t), 2.4 (3H, s), 4.4 (2H, q), 4.9 (2H, s), 6.95 (2H, m) and 8.45 (2H, m); and Anal. Calcd for C$_{15}$H$_{14}$O$_4$N$_2$: C, 62.93% H, 4.93% N, 9.79% and Found: C, 62.58% H, 4.92% N, 9.51%; 1-oxo-5H-pyrimido[2,1-c][1,4]benzothiazine-2-carboxylic acid, ethyl ester: mp 92°–94° C. (crystallized from ethyl acetate-hexane); nmr(CDCl$_3$) δ1.4 (3H, t), 3.8 (2H, s), 4.37 (2H, q), 7.3 (3H, m), 8.05 (1H, m) and 8.5 (1H, s); and Anal. Calcd for C$_{14}$H$_{12}$N$_2$SO$_3$: C, 58.33% H, 4.20% N, 9.72% and Found: C, 58.53% H, 4.17% N, 9.63%.

EXAMPLE 7

1-Oxo-5H-pyrimido[2,1-c][1,4]benzoxazine-2,8-dicarboxylic Acid, Diethyl Ester [I; R$^1$=COOEt, R$^2$=H, R$^3$=Et and X=O]

2-[[N-(7-ethoxycarbonyl-2H-1,4-benzoxazin-3-yl)amino]methylene]propanedioic acid, diethyl ester (15.0 g, 384 mmol, described in Example 5) was mixed with polyphosphoric acid (500 g) so as to render the mixture homogeneous. Then the material was heated at 100° C. in an open beaker for 1 hr. Ice was added to the syrupy reaction mixture and a white precipitate was obtained upon trituration of the yellow mass. The suspension was collected by filtration and dissolved in chloroform. The solution was washed with aqueous potassium carbonate, dried over magnesium sulfate and evaporated to give a white powder of the title compound (8.60 g): mp 114°–116° C.; ir(CHCl$_3$) 1,745, 1,715, 1,596, 1,540 and 1,495 cm$^{-1}$; uv max(CH$_3$OH) 329 ($\epsilon$11,360) and 256 nm($\epsilon$9,657); and Anal. Calcd for C$_{17}$H$_{16}$N$_2$O$_6$: C, 59.30% H, 4.68% N, 8.14% and Found: C, 59.23% H, 4.66% N, 8.11%.

In the same manner, but replacing 2-[[N-(7-ehtoxycarbonyl-2H-1,4-benzoxazin-3-yl)amino-9 methylene]-propanedioic acid, diethyl ester with an equivalent amount of a following compound of formula IV, described in Example 5: 2-[[N-(7-bromo-2H, 1,4-benzoxazin-3-yl)amino]methylene]-propanedioic acid, diethyl ester; 2-[[N-(6-ethyl-7-nitro-2H-1,4-benzoxazin-3-yl)amino]methylene]-propanedioic acid, diethyl ester; 2-[[N-(7-trifluoromethyl-2H-1,4-benzoxazin-3-yl)amino]methylene]-propanedioic acid, diethyl ester; 2-[[N-(6-nitro-2H-1,4-benzoxazin-3-yl)amino]methylene]-propanedioic acid, diethyl ester; 2-[[N-(6-trifluoromethyl-2H-1,4-benzoxazin-3-yl)amino]methylene]-propanedioic acid, diethyl ester; 2-[[N-(6-hexyl-7-propyl-2H-1,4-benzoxazin-3-yl)amino]methylene]-propanedioic acid, diethyl ester; 2-[[N-(7-butyl-6-iodo-2H-1,4-benzothiazin-3-yl)amino]methylene]-propanedioic acid, diethyl ester and 2-[[N-(7-iodo-2H-1,4-benzoxazin-3-yl)amino]methylene]-propanedioic acid, diethyl ester, the following compounds of formula I are obtained, respectively: 8-bromo-1-oxo-5H-pyrimido[2,1-c][1,4]benzoxazine-2-carboxylic acid, ethyl ester; 9-ethyl-8-nitro-1-oxo-5H-pyrimido[2,1-c][1,4]benzoxazine-2-carboxylic acid, ethyl ester; 8-trifluoromethyl-1-oxo-5H-pyrimido[2,1-c][1,4]benzoxazine-2-carboxylic acid, ethyl ester, 9nitro-1-oxo-5H-pyrimido[2,1-c][1,4]benzoxazine-2-carboxylic acid, ethyl ester; 9-trifluoromethyl-1-oxo-5H-pyrimido[2,1-c][1,4]benzoxazine-2-carboxylic acid, ethyl ester, 9-hexyl-8-propyl-1-oxo-5H-pyrimido[2,1-c][1,4]benzoxazine-2-carboxylic acid, ethyl ester; 8-butyl-9-iodo-1-oxo-5H-pyrimido[2,1-c][1,4]-benzothiazine-2-carboxylic acid, ethyl ester and 8-iodo-1-oxo-5H-pyrimido[2,1-c][1,4]benzoxazine-2-carboxylic acid, ethyl ester.

EXAMPLE 8

1-Oxo-5H-pyrimido[2,1-c][1,4]benzothiazine-2-carboxylic Acid, Ethyl Ester, 6-Oxide 1-Oxo-5H-pyrimido[2,1-c][1,4]benzothiazine-2-carboxylic acid, ethyl ester (288 mg, 1 mmol, described in Example 6) was dissolved in methylene chloride (40 ml) and stirred for 18 hr in the presence of 3-chloroperbenzoic (188 mg. 1.1 mmol). The solution was washed with a cold sodium bicarbonate solution, brine, dried over magnesium sulfate and evaporated to yield a pink powder (260 mg) upon trituration with diethyl ether. Recrystallization from ethyl acetate-hexane gave the title compound: mp 165°–167° C.; ir(CHCl$_3$) 1,745 and 1,720 cm$^{-1}$; uv max(CH$_3$OH) 325 nm($\epsilon$9,720); nmr(CDCl$_3$) δ1.4 (3H, t), 4.4 (2H, q), 4.0 and 4.6 (2H, doublets) 7.7 (4H, m) and 8.28 (1H, s); and Anal. Calcd for C$_{14}$H$_{12}$N$_2$O$_4$S: C, 55.26% H, 3.98% N, 9.21% and Found: C, 55.14% H, 3.88% N, 8.88%.

EXAMPLE 9

1-Oxo-5H-pyrimido[2,1-c][1,4]benzoxazine-2,8-dicarboxylic acid, 2-Ethyl Ester [I; R$^1$=COOH, R$^2$=H, R$^3$=Et and X=O]

A solution of 1-oxo-5H-pyrimido[2,1-c][1,4]benzoxazine-2,8-dicarboxylic acid, diethyl ester (3.00 g, described in Example 7) and 50% aqueous potassium hydroxide (70 ml) in ethanol (25 ml) was stirred at 20° C. for 30 min and cooled to 0° C. 2N hydrochloric acid was added until the mixture was acidic. The precipitate was collected and dried to give the title compound (2.51 g): mp 140° C.; ir(nujol) 3,500, 3,460, 2,500, 1,900, 1,740 and 1,703 cm$^{-1}$; and nmr(DMSO-d$_y$) δ1.3 (3H, t), 4.25 (2H, q), 5.1 (2H, s), 7.4 (1H, s) and 8.0 (4H, m).

A solution of the title compound (2.00 g) and benzenemethanamine (0.68 g) in 2-propanol (20 ml) was saturated with diethyl ether. The precipitate was collected and crystallized from methanol-diethyl ether to obtain the benzenemethanamine salt (0.461 g) of the title compound: mp 174°–175° C., ir(nujol) 3,200, 2,700, 1,730, 1,670 and 1,630 cm$^{-1}$; uv max(CH$_3$OH) 332

($\epsilon$10,420) and 254 nm($\epsilon$7,075); nmr(DMSO-d$_6$) $\delta$1.3 (3H, t), 4.0 (2H, s), 4.25 (2H, q), 5.05 (2H, s), 5.55 (73H, s), 7.5 (6H, m) and 8.35 (2H, m); and Anal. Calcd for $C_{15}H_{12}N_2O_6$ $C_7H_9N$: C, 62.40% H, 5.00% N, 9.93% and Found: C, 61.25% H, 4.98% N, 9.53%.

We claim:

1. A compound of formula I

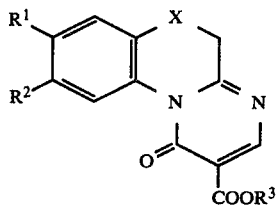

in which $R^1$ is hydrogen, lower alkyl, halo, lower alkoxycarbonyl, carboxy, nitro or trifluoromethyl; $R^2$ is hydrogen, lower alkyl, halo, nitro or trifluoromethyl; $R^3$ is lower alkyl; and X is oxygen; or a therapeutically acceptable basic addition salt of the compound of formula I in which $R^1$ is carboxy and $R^2$, $R^3$ and X are as defined herein.

2. A compound according to claim 1 wherein $R^1$ is hydrogen, lower alkyl, halo, lower alkoxycarbonyl or carboxy; and $R^2$ is hydrogen, lower alkyl or halo.

3. A compound according to claim 1 wherein $R^1$ is hydrogen or lower alkyl; and $R^2$ is hydrogen or halo.

4. 9(1,1-dimethylethyl)-1-oxo-5H-pyrimido[2,1-c][1,4]benzoxazine-2-carboxylic acid, ethyl ester, a compound according to claim 1 wherein $R^1$ is hydrogen $R^2$ is 1,1-dimethylethyl, $R^3$ is ethyl and X is oxygen.

5. 1-Oxo-5H-pyrimido[2,1-c][1,4]-benzoxazine-2,8-dicarboxylic acid, diethyl ester, a compound according to claim 1 wherein $R^1$ is ethoxycarbonyl, $R^2$ is hydrogen, $R^3$ is ethyl and X is oxygen.

6. 1-Oxo-5H-pyrimido[2,1-c][1,4]benzoxazine-2,8-dicarboxylic acid, 2-ethyl ester, a compound according to claim 1 wherein $R^1$ is carboxy, $R^2$ is hydrogen, $R^3$ is ethyl and X is oxygen.

7. 1-Oxo-5H-pyrimido[2,1-c][1,4]benzoxazine-2-carboxylic acid, ethyl ester, a compound according to claim 1 wherein $R^1$ and $R^2$ are hydrogen, $R^3$ is ethyl and X is oxygen.

8. 9-Chloro-1-oxo-5H-pyrimido[2,1-c][1,4acid, ethyl ester, a compound according to claim 1 wherein $R^1$ is hydrogen, $R^2$ is chloro, $R^3$ is ethyl and X is oxygen.

9. 8-Methyl-1-oxo-5H-pyrimido[2,1-c][1,4]benzoxazine-2-carboxylic acid, ethyl ester, a compound according to claim 1 wherein $R^1$ is methyl, $R^2$ is hydrogen, $R^3$ is ethyl and X is oxygen.

10. A method of preventing or treating anaphylactic reactions or allergic conditions in a mammal, which comprises administering to said mammal an effective anaphylactic alleviating or allergic alleviating amount of a compound according to claim 1.

11. A pharmaceutical composition, which comprises a compound according to claim 1 and a pharmaceutically acceptable carrier.

* * * * *

UNITED STATES PATENT AND TRADEMARK OFFICE
CERTIFICATE OF CORRECTION

PATENT NO. : 4,307,092

DATED : December 22, 1981

INVENTOR(S) : Gauthier et al

It is certified that error appears in the above-identified patent and that said Letters Patent are hereby corrected as shown below:

Column 6, line 56, read for the first formula in Reaction Scheme 1, the formula

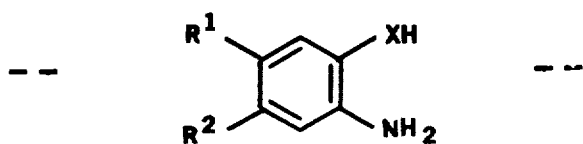

Claim 5, line 3, delete "wherein $R^1$", first occurence;

Claim 8, line 1, "9-Chloro-1-oxo-5H-pyrimido [2,1-c] [1,4acid" should read -- 9-Chloro-1-oxo-5H-pyrimido [2,1-c] [1,4] benzoxazine-2-carboxylic --

Signed and Sealed this

Twenty-first Day of December 1982

[SEAL]

Attest:

GERALD J. MOSSINGHOFF

Attesting Officer

Commissioner of Patents and Trademarks